United States Patent [19]

Campman

[11] 3,950,739

[45] Apr. 13, 1976

[54] DETECTOR FOR DETECTING AND LOCATING THE SOURCE OF A CONTAMINATING GAS OR SMOKE IN THE ATMOSPHERE

[76] Inventor: James P. Campman, 12900 Broadmoore Road, Silver Spring, Md. 20907

[22] Filed: Oct. 30, 1974

[21] Appl. No.: 519,252

[52] U.S. Cl. .......................... 340/237 R; 340/237 S
[51] Int. Cl.² ........................................ G08B 17/10
[58] Field of Search ........... 340/237, 242; 23/254 E, 23/255 E; 73/23, 27

[56] References Cited
UNITED STATES PATENTS

| | | | |
|---|---|---|---|
| 2,499,806 | 3/1950 | Wouk et al. | 340/237 R |
| 3,686,655 | 8/1972 | Kasahara | 340/237 R |
| 3,786,462 | 1/1974 | Hayden | 340/237 R |
| 3,879,717 | 4/1975 | Gruensfelder | 340/237 R |

*Primary Examiner*—John W. Caldwell
*Assistant Examiner*—Daniel Myer

[57] ABSTRACT

The invention involves an apparatus and method. It has for a purpose the detection of a contaminating gas or smoke in the free and unconfined atmosphere and for locating the source of the contamination. A specific use is to detect leaks in systems containing gas under pressure. The apparatus comprises a sensor in the form of a semi-conductor material, whose conductance varies with variations in the density of the contaminant in the region immediately surrounding the sensor. The sensor is connected to the input circuit of an amplifier, which operates to produce a voltage that varies with the conductance of the sensor. For producing an indication of the presence of the contaminating gas and also its density, a pulse generator is connected to and controlled by the voltage output of the amplifier, whereby, as the voltage of the output of the amplifier varies, the frequency of the pulses of the pulse generator also varies. A visual indicator in the form of a light emitting diode is connected to the output of the pulse generator from which a pulsating light is produced which varies in step with the output of the pulse generator. An audible indicator is also provided, which is a tone whose pitch varies with changes in density, which is pulsed at a frequency which also varies in frequency with changes in density of the contaminant. For this purpose, an audio frequency oscillator is connected to the output of the amplifier whereby an audio frequency voltage is produced which varies with the voltage at the output of the amplifier. A speaker is used for converting the audio frequency voltage into a tone whose pitch varies with the audio frequency voltage. A gating device under the control of the pulse generator connects the audio frequency generator to the speaker, which produces the pulsations in the audible signal. The method comprises the steps that are performed by the apparatus for sensing the gas or smoke and producing an indication of its presence and change in density.

2 Claims, 5 Drawing Figures

DETECTOR FOR DETECTING AND LOCATING THE SOURCE OF A CONTAMINATING GAS OR SMOKE IN THE ATMOSPHERE

PRIOR ART

The apparatus of the present invention incorporates and utilizes a Taguchi gas sensor as an element thereof. The sensor is disclosed in the Taguchi U.S. Pat. Nos. 3,631,436 and 3,695,848.

It consists of a sintered semi-conductor of metallic oxide, which has an affinity for the oxygen in the atmosphere, and in the presence of an uncontaminated atmosphere at a predetermined temperature will exhibit a definite resistance. The presence of an adsorbed oxygen molecule establishes an immobilizing positive charge to a conductive electron in the semi-conductor and the density of the adsorbed molecules thus determines the resistance of the semi-conductor.

The semi-conductor has associated therewith one or two heater coils for heating the semi-conductor to a temperature above a normally expected ambient temperature of the atmosphere where the apparatus is to be used, to maintain a stable operating temperature for the semi-conductor. The coils also serve as connecting electrodes between the semi-conductor and the rest of the circuitry of the apparatus.

The temperature of the semi-conductor also affects its resistance, because the higher operating temperature will increase the population of the conduction electrons in the semi-conductor and as the temperature rises, with a constant density of oxygen molecules the resistance would decrease. Therefore it is necessary to establish a stable operating temperature for the semi-conductor to eliminate variations of the resistance due to the temperature.

When a contaminating gas or smoke enters the atmosphere, particularly one that is deoxidizing in character, the number of adsorbed oxygen molecules on the semi-conductor is decreased, in substantial proportion to the amount of contaninating gas in the atmosphere in the region of the semi-conductor, thus decreasing the resistance of the semi-conductor by reducing the immobilizing positive charge on the semi-conductor. Thus more of the captive electrons are liberated and the resistance is decreased.

There is a wide variation in the resistance of the semi-conductor with changes in density of the contaminating gases. As between gases of different character there is also a variation between the density and the resistance that it causes. In the prior art structure, it has been found for the benefit of optimum sensitivity that a different sensor element is desired as differmetallic oxides have different responses, and different ranges of variation of the resistance.

The range of variation of the resistance is so great that as a rule, in the prior devices no amplification of the output of the sensor is required.

In the prior art devices and apparatus for use in determining variations in density or concentration of contaminating gases or smoke, a series of samples of the atmosphere is taken at different time intervals. The indications, usually from a meter, are compared to determine the change in the density. In the search procedure, the samples are taken from different points and the readings are compared to determine the change in density and the direction of the density gradient between the two points. From these reading the direction toward the source of the contamination is determined.

These prior art devices have been slow in response to variations in the density of the contaminating gases or smoke and small variations in density would not be perceptible in the reading of the meter. They are practically useless for the purpose of locating the source of the contamination except in the hand of one skilled in its utilization.

The present invention makes use of the Taguchi gas sensor because of its wide range of response and its capability for fast changes to variations of the density of the contaminants. The present invention therefore is considered an improvement over that disclosed by Taguchi and other prior art devices such as the hot wire type.

In the present invention, the signal from the Taguchi gas sensor is amplified whereby, extremely low densities of gases or smoke detected by the sensor is made into a more perceptible signal. The amplifier produces an amplified signal that is used to control the frequency of an oscillator, which is more sensitive to variations in voltage than meters. The output from the oscillators is utilized to produce a visual and audible signal, pulsating at a frequency dependent upon the density of the contaminant. The audible signal is a tone, the frequency which varies with the density of the contaminant. From particularly the audible signal, it is possible to detect very slight changes in density of the contaminant. From the frequency of the pulses larger changes of the density of the contaminant is perceptible. Thus the one using the apparatus does not need to watch a meter to be aware of changes in density. The frequency of the tone and the pulses will indicate such changes and he can direct his sole attention to where the apparatus is being directed.

No special skill is needed on the part of the user of the instrument. There are but two controls one to turn on the power and the other to adjust the sensitivity of the apparatus when it is required.

The apparatus is easily handled and transported. It can be carried in a pocket of ones clothing. It has a flashlight type casing providing a recess for protecting the sensor from damage and to form a small chamber in which the sensor is located and to which the contaminated atmosphere can be transported by a probe means. The simplicity of the apparatus and cost puts the apparatus within the reach of every house holder, trailorite, boatsman, mechanic, and repairman, making their work easier and providing for greater safety.

The object of the present invention is to provide a more sensitive gas and smoke detector, or one that is capable of sensing very small concentration of a contaminating gases or smoke in the atmosphere.

Another object of the invention is to provide apparatus that provides a signal the character of which changes with changes in the density of the comtaminants whereby the density gradient can lead the user to the source of the contaminants.

Still another object is to provide apparatus capable of being housed in a small hand held casing and one that requires no particular skill from the user to obtain the desired information.

Another object is to provide an apparatus inexpensive to produce and within the reach of the average home owner as a means for assuring their greater safety.

3

Other objects of the invention will become obvious as the disclosure proceeds.

DRAWINGS

DESCRIPTION OF INVENTION

The apparatus includes a sensory element for responding to a variation in density or concentration of a gas or smoke, a circuitry included on printed circuit boards, resistors, capacitors, a potentiometer, a switch for controlling the application of power and batteries all incased in a flashlight type casing that makes for ease of transportation and utilization.

Figure 1:
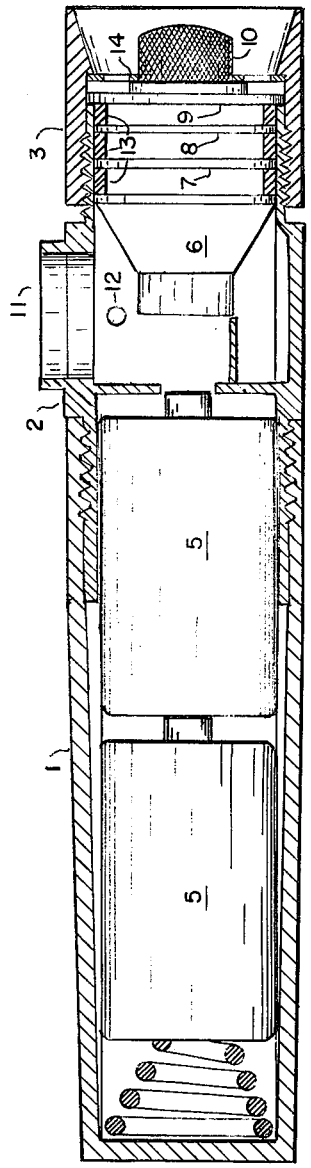
FIG. 1 is a sectional view of the apparatus incased in a flashlight type casing for disclosing the principal components and their placement.

Referring to FIG. 1, the casing is divided into three sections. Section 1 has a closed end housing a tapered spring for engaging an end of one of the batteries 5. The opposite end of section 1 is internally threaded to engage with externally threaded end of the midsection 2. The midsection 2 has a transverse opening 11, below which is to be located a switch and through which extends its actuator. A light emitting diode is to be housed in the hole 12 of the casing and the side of the casing opposite the hole 12 (not seen in FIG. 1) is to have a similar hole through which a small screw driver can be inserted to adjust a potentiometer. The potentiometer and switch would be attached to each other and located under the opening 11. They are not disclosed in FIG. 1, for the purpose of simplicity of the disclosure.

To the right of the opening 11 is a speaker 6 for producing an audible signal indication, circuit boards 7 and 8 and a sensory element mounting board 9 which are spaced apart in the casing by rings 13. The mounting board 9 has spaced apertures for the pins of the sensory element 10 and has a diameter which is the same as the right end of the midsection 2 and is arranged to be clamped against the right end of the midsection 2 by the bezel 14 which engages the sensory element and by which is engaged by the section 3. Section 3 is internally threaded to engage the exterior thread on the right end of the midsection 2 and to clamp the parts in place. A yieldable spacer may, if desired, be inserted about the midsection 2 between a shoulder thereof and the left end of section 3 to permit a firmness of clamping by section 3.

Figure 4:
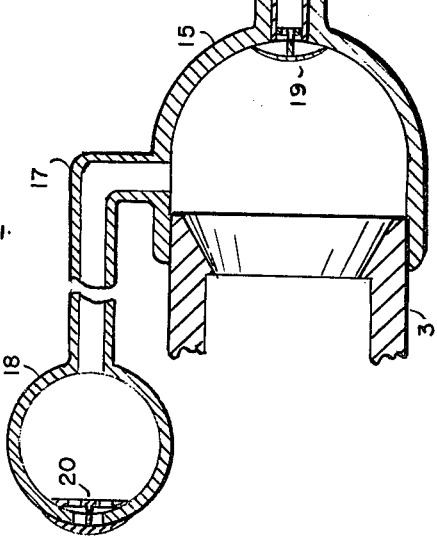
FIG. 4 is a sectional view of a probe means which may be attached to the casing of the apparatus shown in FIG. 1.

The Taguchi gas sensor 10 is plugged into the board 9 and is clamped in place by the bezel 14 which engages a flange on the sensor which is in turn engaged by an interior flange of section 3. The Taguchi sensor has a fine stainless steel wire mesh covering the sensory element which will prevent ignition of gases exteriorly of the mesh by ignition of the gases within the mesh cap. The section 3 extends beyond the end of the mesh cap of the sensor and thus afords protection to the sensor against damage. The space within the section 3 surrounding the sensor provides a chamber when the probe of FIG. 4 is attached thereto. The components such as the resistors, capacitors, transistors and IC component, which are mounted on the boards, are not disclosed thereon for simplicity of disclosure.

Figure 2:
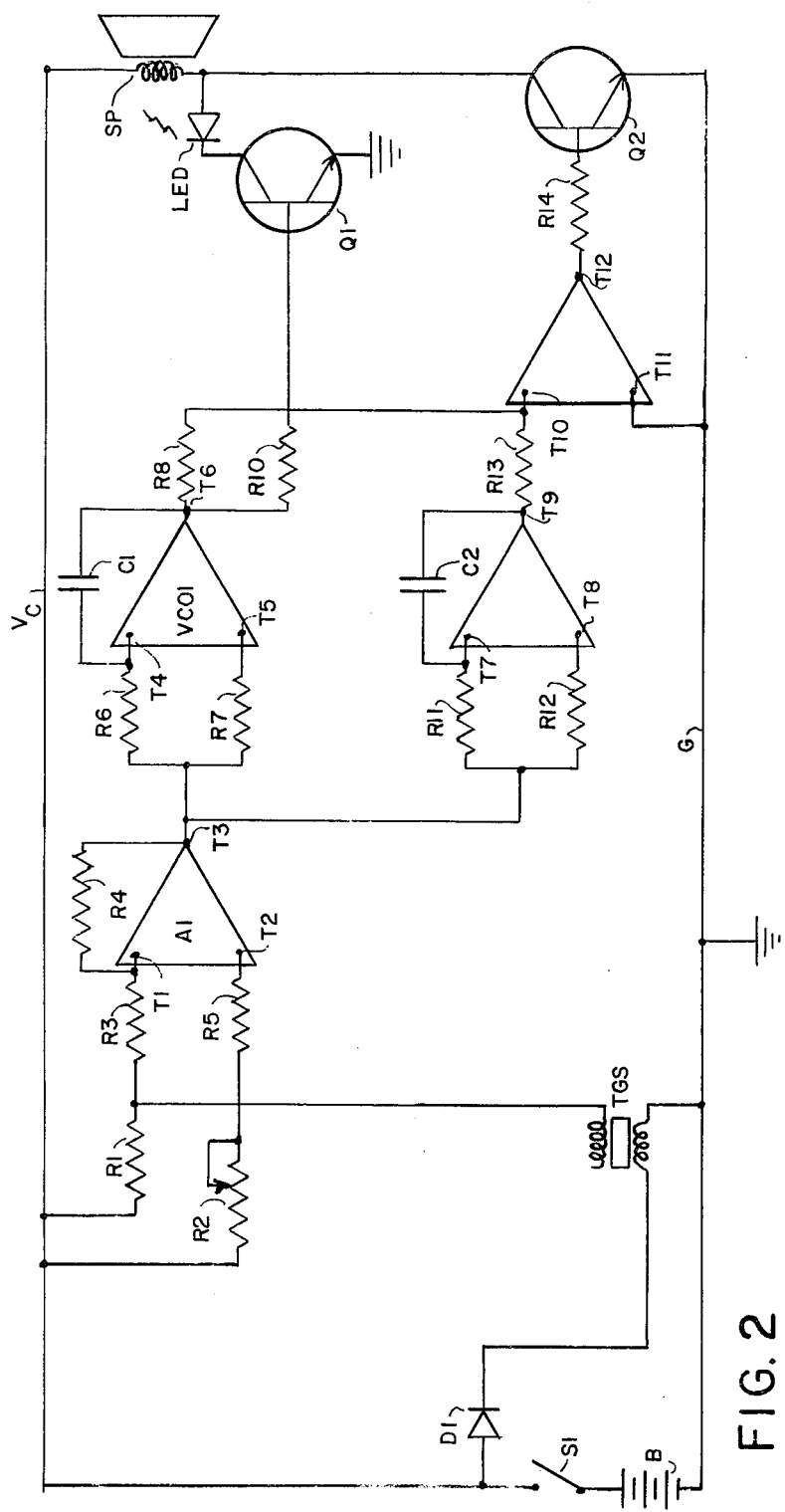
FIG. 2 is a schematic view of the circuitry of the portable model of the apparatus shown in FIG. 1.

Refferring to FIG. 2, the Taguchi gas sensor TGS is shown as connected between the busses $V_c$ and G in series with the resistor R1. When the Switch S1 is closed the busses are energized by the battery B composed of two cells as seen in FIG. 1. Together, the two cells provide about three volts. The sensor TGS connected in series with resistor R1 forms therewith a voltage divider. One of the coils of the sensor TGS is connected through diode D1 to the positive side of the battery B through switch S1 so that when the switch S1 is closed to energize the circuitry, the semi-conductor of the TGS sensor is heated.

The circuit between the resistor R1 and the sensor TGS is connected through resistor R3 to terminal T1 of the amplifier A1. Terimnal T2 of the amplifier A1 is connected through resistor R5 and potentiometer R2 to the buss $V_c$ and the output terminal T3 of amplifier A1 is connected back through resistor R4 to terminal T1 to form a feed back circuit for the amplifier.

The amplifier A1 is of the differential type having dual input terminals T1 and T2. Terminal T2 is connected through the potentiometer R2 to the constant voltage Buss $V_c$ and the voltage on terminal T2 stays the same, except when the potentiometer is adjusted. Terminal T1 is the inverting input and terminal T2 is the noninverting input. This means that when the voltage on terminal T1 varies relative to that on terminal T2, terminal T1 may have the dominant voltage or terminal T2 may have the dominant voltage. When the voltage on terminal T1 is dominant, the voltage on the output terminal would be zero. When the voltage on terminal T2 is dominant there will be a voltage on the output terminal T3 which is proportional to the difference between the voltages on the terminal T1 and T2. The voltage on terminal T1 is under the control of the Taguchi gas sensor and varies as the resistance of the sensor varies with changes in density of contaminating gases in the atmosphere around the sensor.

The output terminal T3 of the amplifier A1 is connected through resistors R6 and R7 respectively to the terminals T4 and T5 of the pulse Generator VCO1. The output terminal T6 of the pulse Generator VCO1 is coupled back through capacitor C1 to terminal T4 and this constitutes a feedback circuit to provide for the oscillations. The pulse generator has two modes of operation, a static mode in which there is no oscillation producing a unvarying voltage at terminal T6 and a dynamic mode in which there is oscillation producing a pulsating voltage at terminal T6. The determination of the mode of operation of the pulse generator VCO1 is the voltage applied on the terminals T4 and T5, which also determines the frequency of the pulse generator. The pulse generator has a threshold voltage below which the pulse generator operates in its static mode and above which the pulse generator operates in its dynamic mode. Changes in temperature of the pulse generator affects the threshold voltage. Occasionally it is necessary to adjust the voltage applied to the input of the oscillator to correct for the change in the threshold voltage. This change in voltage is effected by the adjustment of the potentiometer R2.

The object in the adjustment of the potentiometer R2 is to adjust the output of the amplifier relative to the threshold voltage of the amplifier such that the pulse generator is at its threshold voltage but in its static mode of operation and so that any upward change in the voltage from the amplifier due to variation of the resistance of the Taguchi gas sensor will start the oscillator to switch to its other mode of operation at a frequency that is dependent upon the amount of upward change in the voltage at the output of the amplifier A1. The potentiometer is therefore both a sensitivity and a threshold control device. The frequency band for the pulse generator is from zero to approximately thirty cycles per second.

The output terminal T6 of the pulse generator VCO1 is connected through resistor R10 to the base of the transistor Q1, whose emitter is connected through ground to the buss G. The collector of transistor Q1 is connected through a light emitting diode LED and through the coil of the speaker SP to the buss $V_c$. Thus when the pulse generator is in its static mode of operation the light emitting diode produces a steady light and when the pulse generator is in its dynamic mode of operation the light emitting diode produces a pulsating light at the frequency of the oscillator.

The light emitting diode operates to produce an indication of three conditions. When the switch S1 is turned on and there is no light from the light emitting diode, it is an indication that there is a failure of power supply, either that the batteries are dead or that there is an open circuit. After the switch is turned on, there would normally be a pulsating light emitted from the diode indicating that the apparatus is in its warm up state. It requires from one to three minutes for the sensor to be heated to its stable operation temperature. If after a period of three minutes the light still pulsates, it indicates a need for an adjustment of the potentiometer to bring the voltage at the output of the amplifier A1 to a point just below the threshold voltage of the pulse generator. At the time this occurs the pulsations and the pulse generator returns to its static mode of operation and the apparatus is then ready for use in detecting the presence of a gas or smoke. When there is a contaminating gas or smoke in the atmosphere surrounding the sensor the light will again start pulsating indicating the presence of the contaminant. However, one cannot perceive a change in the frequency of the pulsating light as easily as one can perceive the same changes in an audible signal. The apparatus is thus provided with a means for producing an audible signal that is issued in pulses in step with the pulses from the pulse generator VCO1 and a tone that varies with changes in the voltage at the output of the amplifier A1.

For this purpose, output terminal T6 of pulse generator VCO1 is also connected through resistor R8 to terminal T10 of gating amplifier A2, which has its terminal T11 connected to the buss G. The output terminal T12 is connected through resistor R14 to the base of transistor Q2, whose collector-emitter circuit is in series with the coil of the speaker SP between the busses $V_c$ and G. When there is a voltage on the terminal T6 of the pulse generator there is a voltage applied to the terminal T10 which produces a zero voltage on the base of the transistor Q2 which renders it non-conductive, a condition for the silent state of the speaker. When there is no voltage on the terminal T10, there will be a voltage on the base of the transistor Q2 which will make it conductive to thus complete the connection of the coil of the speaker between the busses $V_c$ and G.

For producing a tone from the speaker when in its on state, requires an audio frequency input to the speaker circuit. This is provided by the oscillator VCO2. The audio frequency oscillator has its input terminals T7 and T8 connected respectively through resistors R11 and R12 to the output terminal T3 of the amplifier A1. Its output terminal T9 is connected back to terminal T7 through the capacitor C2 that causes the production of oscillations. Terminal T9 is further connected through resistor R13 to terminal T10 of the gating amplifier A2 and thus provides the audio frequency for the speaker.

In this embodiment of the invention, the gating operation of the amplifier A2 connects the oscillator VCO2 through to the base of the transistor Q2 and simultaneously amplifies the output from the oscillator VCO2 to the value required for the operation of the speaker SP. The change in the frequency of the pulses in tone from the speaker will be indicative of rather large changes in the density of the contaminant in the region of the sensory element. The change in the frequency of the tone during the pulses will be indicative of large and small changes in the density, in density of the contaminants. The change in the tone is more perceptible than the changes in the frequency of the pulses and also more perceptible than changes in position of the pointer on a meter. The change in the density indication is an important factor in locating the source of the leak of the contaminating gases or source of the smoke. Its actual change in magnitude is relatively unimportant. The response to change and the ability to indicate very small changes in density is of importance in the utilization of the apparatus as a search tool. The improvement of the apparatus for providing a sensitive search instrument has resulted also in a very sensitive gas detector, capable of detecting very low density gases in the region of a few parts per million.

The embodiment of FIGS. 1 and 2 operates as follows. When the TGS is cold its conductivity is comparatively low. At the instant of the closure of the switch S1 there is a surge of current through the circuit of the sensor and the resistor R1 that produces a substantial voltage drop across the resistor R1 whereby the voltage on the terminal T2 will be the dominant voltage. At the instant the switch S1 is turned on the heater coil of the sensor TGS begins to warm up. The pulse generator VCO1 starts to oscillate to activate the light emitting diode LED and the speaker SP. As the sensor is heated the frequency of the pulses and the tone of the speaker decreases to the point where they cease and the pulse generator VCO1 begins its static mode of operation.

When this happens, the audible tone ceases and the pulsations on the visual indicator, the light emitting diode, ceases and the apparatus is ready for utilization as a detector and search instrument. The audible tone ceases because, at the time the pulse generator VCO1 is in its static mode of operation the output therefrom causes the light emitting diode to be continually in its "on" state and when this same output from the pulse generator VCO1 is applied to the inverting terminal T10 of the amplifier A1 no voltage appears at its terminal T12. Thus the audible signal is silenced.

When the sensory element is then thereafter exposed to an atmosphere that has a contaminating gas or smoke in it, that has the effect of reducing the charge on the sensor, the sensor has a change in resistance which causes a change in the voltage on the terminal T1 of the amplifier A1. This change in voltage, results in a change in the output voltage from the amplifier A1 and on the mode of operation and frequency of the pulse generator VCO1. The frequency of the pulse generator and of the audio oscillator VCO2 changes with the change in the voltage applied to their inputs and there will be a pulsating signal from both the visual and audible signal producing means the light emitting diode and the speaker. The frequency of the pulses and the frequency of the audio tone will both change in response to the change in density of the contaminating gases in the region of the sensory element.

To find the source of the contaminant, the sensory element of the apparatus is moved from point to point while listening to the audible tone. A higher pulse frequency or increase in the frequency of the tone indicates that the sensory element is being moved in the direction of the source, because as one moves from a point toward the source, the density of the gases will become greater. On the other hand should the sensory element be moved in a direction away from the source the density would decrease and the tone's frequency would decrease indicating that the direction of movement of the sensor must be changed to the opposite direction of motion. If there is no change in the frequency of the tone or pulsations, it indicates that the sensor is probably being moved at right angles to the density gradient and that the direction of motion of the sensory element should be moved at right angles to the previous motion.

For utilization of the apparatus it is important that it be a highly sensitive and readily responsive to changes in density. The rate of response of the sensory element is dependent on the temperature at which it is operated. A low temperature produces a sluggish response whereas a higher operating temperature produces an improvement in the rate of response. The upper limits of operating temperature is in the region of 300° Fahrenheit.

Figure 5:
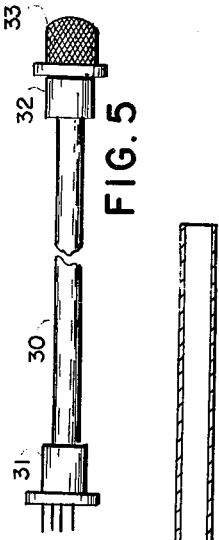
FIG. 5 is a plan view of another form of the probe means whereby the sensor element can be placed in comparatively inaccessible places.

In the use of the apparatus as a search instrument to locate leaks in a system containing a dioxidizing gas or the like, it is sometimes difficult to place the sensory element close enough to pin point the leak. To permit the more inaccessible places to be reached a probe is required, either to draw the atmosphere from the inaccessible places and place in the region of the sensory element or to enable the sensory element to be inserted into the inaccessible places. FIGS. 4 and 5 disclose two embodiments of probes for this purpose.

In FIG. 4 the probe comprises a bulb-like closure member 15 having a pipe member 16 connected thereto through which the atmosphere in a closely confined space may be sampled for testing. The closure member 15 is connected to a compressible bulb means 18 having an exhaust valve 20. The inner end of the pipe member is associated with an intake valve 19 through which the sample of the atmosphere is drawn when the bulb 18 is compressed and released. The bulb-like member 15 fits over the end of the section 3 of the casing and forms therewith a chamber surrounding the sensory element. This type of arrangement is admittedly old in the art.

FIG. 5 shows a second type of probe having a cable with at least four conductors, a four terminal 31 on one end for plugging into the sensor recepticle in the member 9 and a recepticle 32 into which the sensor element may be received and by which the sensor element can be connected to the circuitry within the casing 1–3. In this embodiment the sensory element can be inserted into more confined spaces than would be possible to reach with the apparatus of FIG. 1 alone.

The apparatus is capable of being used as a monitoring detector for confined spaces where there is a danger of gases contaminating the atmosphere thereof. The embodiment of the invention is disclosed in FIG. 3. The circuitry is approximately the same as that shown in FIG. 2 except for the difference in power supply and the extra provisions needed with the different power supply.

The battery powered embodiment could be energized for about ten hours continual service and longer when the service is intermittent as would naturally be the case in a portable device. When a continuous monitoring operation is desired it is necessary to utilize a source having a continual supply of energy being supplied thereto.

Figure 3:
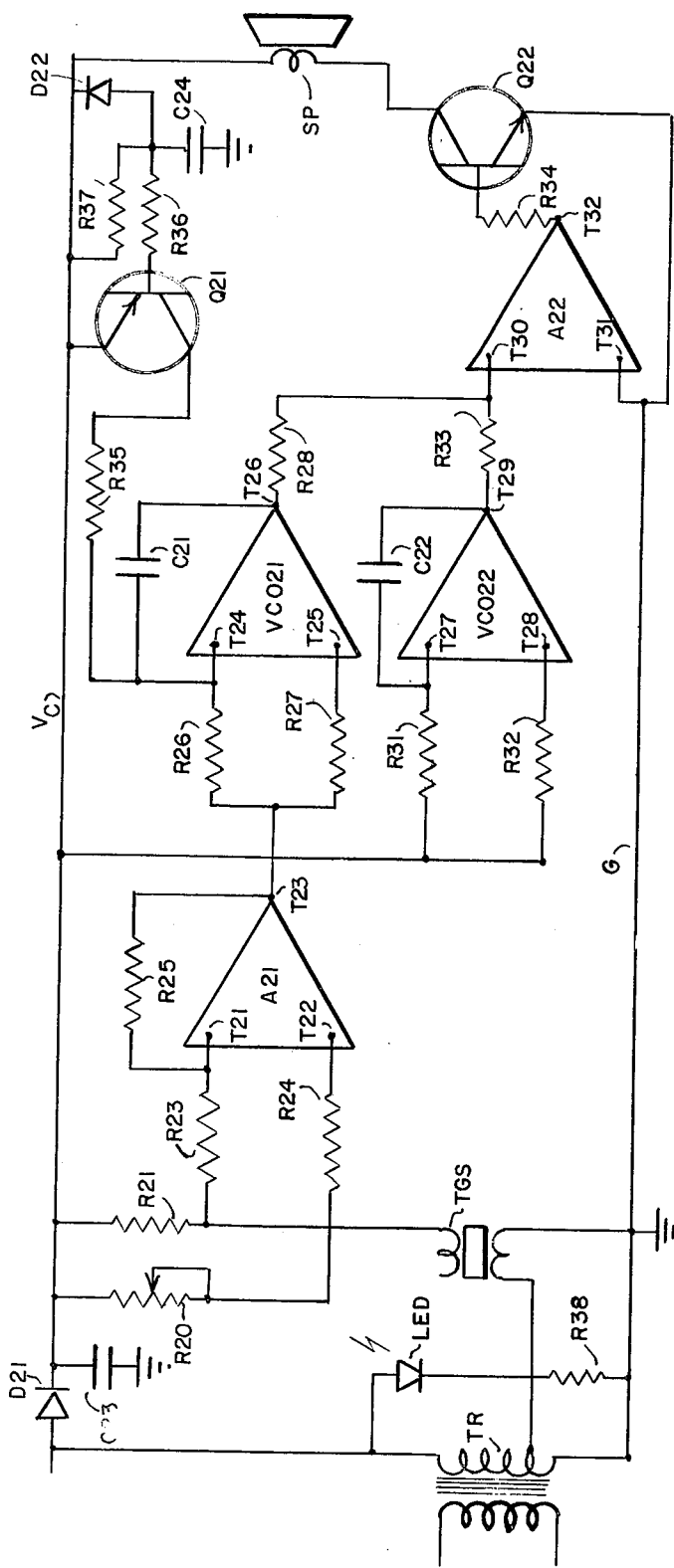
FIG. 3 is a schematic view of the circuitry of the embodiment of the invention used for fixed installations.

In FIG. 3 the source is from the power lines which is reduced from the normal 115 volts AC to about six volts AC. The transformer has its secondary winding connected between the busses $V_c$ and G in series with a rectifier comprised of the diode D21 and the capacitor C23. There is no switch for the control of the supply of power to the transformer Tr it being understood that the line to the primary winding of the transformer would naturally contain such a switching means.

In FIG. 3, the sensory element TGS is connected in series with resistor R21 between the busses $V_c$ and G and through resistor R23 to the terminal T21 of the amplifier A21. Terminal T22 is connected through resistor R24 and potentiometer R20 to the buss $V_c$. The potentiometer is utilized to adjust the output of the amplifier A21 to the threshold voltage of the pulse generator VCO21. The amplifier has a feed back circuit between the terminals T23 and T21, including a resistor R25. The output terminal T23 is connected to terminals T24 and T25 respectively through resistors R26 and R27. The output terminal T26 is coupled through capacitor C21 to the terminal T24 providing a feed back circuit for obtaining oscillations. As in the previously disclosed embodiment, the frequency of the pulse generator and its mode of operation is determined by the voltage applied to its input terminals T24 and T25.

The output terminals T26 is connected through resistor R28 to terminal T30 of the gating amplifier A22, which has its other input terminal connected directly to the buss G. The output terminal T32 is connected through resistor R34 to the base of the transistor Q22 that has its collector-emitter circuit in series with the coil of the speaker SP across the busses $V_c$ and G.

As in the preceding embodiment the pulse generator VCO21 produces voltage pulses while in its dynamic state or mode of operation, the frequency of which has a range from zero to about thirty cycles per second. In its static mode of operation, it produces a constant voltage or zero frequency of operation. When there is a voltage applied from the output of the pulse generator VCO21 to the terminal T30 of the gating amplifier A22 there will be a zero voltage applied to the base of the transistor Q22 and it will be nonconductive. When there is a zero voltage applied on the terminal T30, a voltage will be applied to the base of the transistor Q22, making it conductive, to energize the speaker.

An audio frequency oscillator VCO22 has its input terminals T27 and T28 respectively connected through resistors R31 and R32 to the constant voltage buss V.

The output terminal T29 of the oscillator VCO22 is connected through capacitor C22 to the terminal T27 and through resistor R33 to the terminal T30 of the gating amplifier A22. The input of the oscillator VCO22 being connected to a voltage source that is constant, will operate at substantially constant frequency. When the gating amplifier connects the oscillator VCO22 to the transistor Q22, the speaker will produce pulses of a constant tone. Thus, in the operation of this embodiment, the output of the speaker will be pulses of tones that are constant in frequency. The frequency of the pulses will be determuned by the frequency of the pulse generator VCO21.

When a power source such as is provided from the power lines is used, it is subject to interruption. When this occurs, the temperature of the sensory element changes and to bring it back up to the stable operating temperature without the accompanying alarm signal, requires that there be a delay means provided to prevent the speaker from sounding during the heating up of the sensor.

This delay function is provided by the circutry that includes the transistor Q21. The transistor Q21, when conductive applies through resistor R35, a voltage on terminal T24 of the pulse generator VCO21, which operates to stop or prevent pulse generator, or to put the oscillator in its static mode of operation. A constant voltage is thus provided at its output, which when applied to the terminal T30 of the gating amplifier A22 renders the transistor Q22 nonconductive. The transistor Q21 has its base connected through resistors R36 and R37 and through diode D22 to the buss $V_c$. The junction between the resistor R36 and the diode is connected through capacitor to ground.

When there is a power failure the charge on the capacitor C24 is dumped through the diode D22. When the power is returned the capacitor C24 begins to charge and while it is charging there will be an emitter to base current to render the transistor Q21 conductive to apply a voltage to terminal T24 and thus prevent the pulse generator VCO21 from oscillating. When the capacitor C24 becomes charged the base to emitter circuit becomes nonconductive and the transistor becomes nonconductive. By that time, the sensory element has heated up to its stable operating temperature and in the absence of the contaminating gas necessary to trigger the alarm the oscillator will remain in its static mode of operation.

In the fixed installations and systems it is not necessary to provide the visual indication, as it is very unlikely that any one would be constantly watching the light emitting means. The light emitting means LED provided in series with resistor R38 across the secondary of the transformer will indicate only that the power to the system is either on or off.

With this embodiment the change in density in the monitored space would be indicated only by a change in the frequency of the pulses of the audio tone from the speaker. If it is desired, for greater density change indication the audio oscillator in this embodiment can also be connected to the output of the amplifier A21 so that the tone changes with the change in density also.

The present apparatus as has been stated is merely an indicator of the presence of a contaminating gas or smoke. It is not a measuring device. It is intended to indicate also the change in density of the contamination. This feature enables it to be readily used in the search and location of the source of the contamination.

It is a useful tool for mechanics who work with air conditioners. refregerators, and other gas using apparatus. It is a useful means to be installed in the basement of homes, schools and other public buildings where there is a danger of fire. It is a means for use in industry such as steel mills where they are troubled with carbon monoxide, and in mines where there is apt to be explosive or asphysiating gases.

It is easily transported on one person to indicate when one is entering a place where gas is present. It is comparative inexpensive and within the reach of everyone who would have a need for such knowledge as it provides about the atmosphere. The device is required for ones safty in pleasure vehicles such as travel trailors and motor boats where there is not only gasolene fumes but also propane fumes. The apparatus has many uses to many to enumerate and it has experienced wide range acceptance by those who have seen and used it.

Having disclose my invention, it mode of operation and purpose and its utility what I declare to be my invention is set forth in the following claims.

I claim:

1. The process of detecting and indicating the presence and changes in density of a contaminating gas or smoke in the free and unconfined atmosphere comprising the steps of:

Sensing said contaminating gas or smoke present in the free and unconfined atmosphere and producing voltages that vary with and in proportion to the change in density of said contaminating gas or smoke;

Producing a pulsating voltage whose frequency varies with aforesaid voltage variations and in proportion thereto;

Producing a visual indication consisting of a pulsating light that pulses in step with said pulsating voltage; producing an audio frequency voltage whose frequency varies with aforesaid voltage variations and in proportion thereto Producing pulsations in said audio frequency voltage in step with said pulsating light; and Converting said pulsating audio frequency voltage to a pulsating audible tone whereby there is a continual indication of the presence of gas or smoke and changes in density of the contaminating gases or smoke in the atmosphere in the frequency of the tone and the frequency of the pulsations of the tone.

2. Apparatus for detecting and indicating variations in density of a contaminant in the free and unconfined atmosphere comprising in combination;

A sensory element responsive to variations in the density of the contaminant in the free and unconfined atmosphere in the region of the same and for producing a voltage which varies inversely with said variations in density;

An amplifier for inverting and amplifying said voltage variations;

A pulse generator connected to and controlled by the variations in the voltage from said amplifier to produce pulses whose frequency varies with said voltage from said amplifier;

A light emitting diode connected to and controlled by said pulse generator for producing pulsations of light from said light emitting diode in step with pulses from said pulse generator;

An audio frequency oscillator connected to said amplifier and controlled thereby to produce an audio frequency voltage which varies with the voltage variations in the output of said amplifier;

A speaker for converting audio frequencies to an audible tone whose frequency varies with said audio frequency; and A gating means connected to said pulse generator and controlled thereby and operable to connect said audio frequency oscillator to said speaker to produce pulses in the varying tone whereby an audible signal will be produced whose pitch and pulsations vary with variations of the density of the contaminant.

* * * * *